United States Patent
Sato et al.

[11] Patent Number: 5,475,078
[45] Date of Patent: Dec. 12, 1995

[54] FLUORINATED ORGANOSILICON COMPOUND

[75] Inventors: Shinichi Sato; Takashi Matsuda; Kouji Takano; Toshio Takago, all of Annaka, Japan

[73] Assignee: Shin-Etsu Chemical Co., Ltd., Tokyo, Japan

[21] Appl. No.: 63,743

[22] Filed: May 20, 1993

[30] Foreign Application Priority Data

May 21, 1992 [JP] Japan .................................. 4-154438

[51] Int. Cl.$^6$ .................................................. C08G 77/24
[52] U.S. Cl. .................. 528/16; 528/25; 528/29; 528/31; 528/42; 556/431; 556/471; 556/487
[58] Field of Search .................. 528/16, 25, 29, 528/31, 42; 556/431, 471, 487

[56] References Cited

U.S. PATENT DOCUMENTS

| | | | |
|---|---|---|---|
| 3,627,801 | 12/1971 | Pierce et al. | 528/42 |
| 4,057,566 | 11/1977 | Carter et al. | 260/448.2 |
| 4,100,136 | 7/1978 | Carter et al. | 528/11 |
| 4,968,828 | 11/1990 | Yamamoto | 556/448 |

FOREIGN PATENT DOCUMENTS

| | | |
|---|---|---|
| 514270 | 11/1992 | European Pat. Off. . |
| 2337731 | 8/1977 | France . |
| 1211593 | 8/1989 | Japan . |

OTHER PUBLICATIONS

Chemical Abstracts No. 218903z, vol. 112, 1990, "Fluorine–Containing Silyl Compounds for Polymers", Izeki et al., p. 106.

Chemical Abstracts No. 157678f, vol. 112, 1990, "Fluorine–Containing Ethers as Cross–Linking Agents and Monomers", Izeki et al. p. 667.

Chemical Abstracts No. 93654m, vol. 106, 1987, "Dry Process Lithographic Ink Repellants", Daikin Kogyo Co., Ltd., p. 609.

Jul. 30, 1993 Search Report and Annex, EP 93 10 8185.

Kim et al. J. Fluorine Chem., 1(2), 203–18 (1971).

*Primary Examiner*—George F. Lesmes
*Assistant Examiner*—Helen F. Lee
*Attorney, Agent, or Firm*—Finnegan, Henderson, Farabow, Garrett & Dunner

[57] ABSTRACT

A novel fluorinated organosilicon compound, exhibiting excellent solvent resistance, chemical resistance and mold release, which is represented by general formula (1):

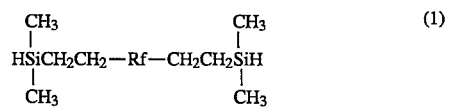

wherein Rf is a divalent group represented by general formula (2):

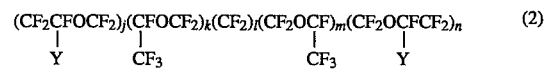

wherein Y is a fluorine atom or $CF_3$ group; l is an integer of 0–8; k and m are integers of 0–4; j and n are integers of 0 or 1; except when j=k=l=m=n=0.

7 Claims, 3 Drawing Sheets

FLUORINATED ORGANOSILICON COMPOUND

BACKGROUND OF THE INVENTION

The present invention relates to a novel fluorinated organosilicon compound.

Fluorinated organosilicon compounds are known to be useful crosslinking agents, or useful starting materials for solvent-resistant or chemical-resistant rubber materials, and those for mold release materials.

SUMMARY OF THE INVENTION

It is an object of the present invention to provide a novel fluorinated organosilicon compound which is extremely useful for the above applications.

There is provided by the present invention a fluorinated organosilicon compound represented by general formula (1) below:

$$\begin{array}{cc} CH_3 & CH_3 \\ | & | \\ HSiCH_2CH_2-Rf-CH_2CH_2SiH \\ | & | \\ CH_3 & CH_3 \end{array} \quad (1)$$

wherein Rf is a divalent perfluoroalkylene group or a divalent perfluoropolyether group represented by general formula (2) below:

$$\begin{array}{c} (CF_2CFOCF_2)_j(CFOCF_2)_k(CF_2)_l(CF_2OCF)_m(CF_2OCFCF_2)_n \\ | \quad\quad | \quad\quad\quad\quad | \quad\quad | \\ Y \quad\quad CF_3 \quad\quad\quad\quad CF_3 \quad\quad Y \end{array} \quad (2)$$

wherein Y is a fluorine atom or $CF_3$ group; l is an integer of 0–8; k and m are integers of 0–4; j and n are integers of 0 or 1, except when j=k=l=m=n=0.

In the fluorinated organosilicon compound of the present invention, there are two silylethylene groups. Since each silylethylene group has a structure that a Si atom is linked, through an ethylene group, to a divalent perfluoroalkylene group or a divalent perfluoropolyether group, the fluorinated organosilicon compound of the present invention exhibits excellent properties, such as solvent resistance, chemical resistance, and mold release, and it permits manufacturing therefrom, materials such as a variety of rubbers, with improvements in their properties.

DETAILED DESCRIPTION OF THE INVENTION

Figure 1:
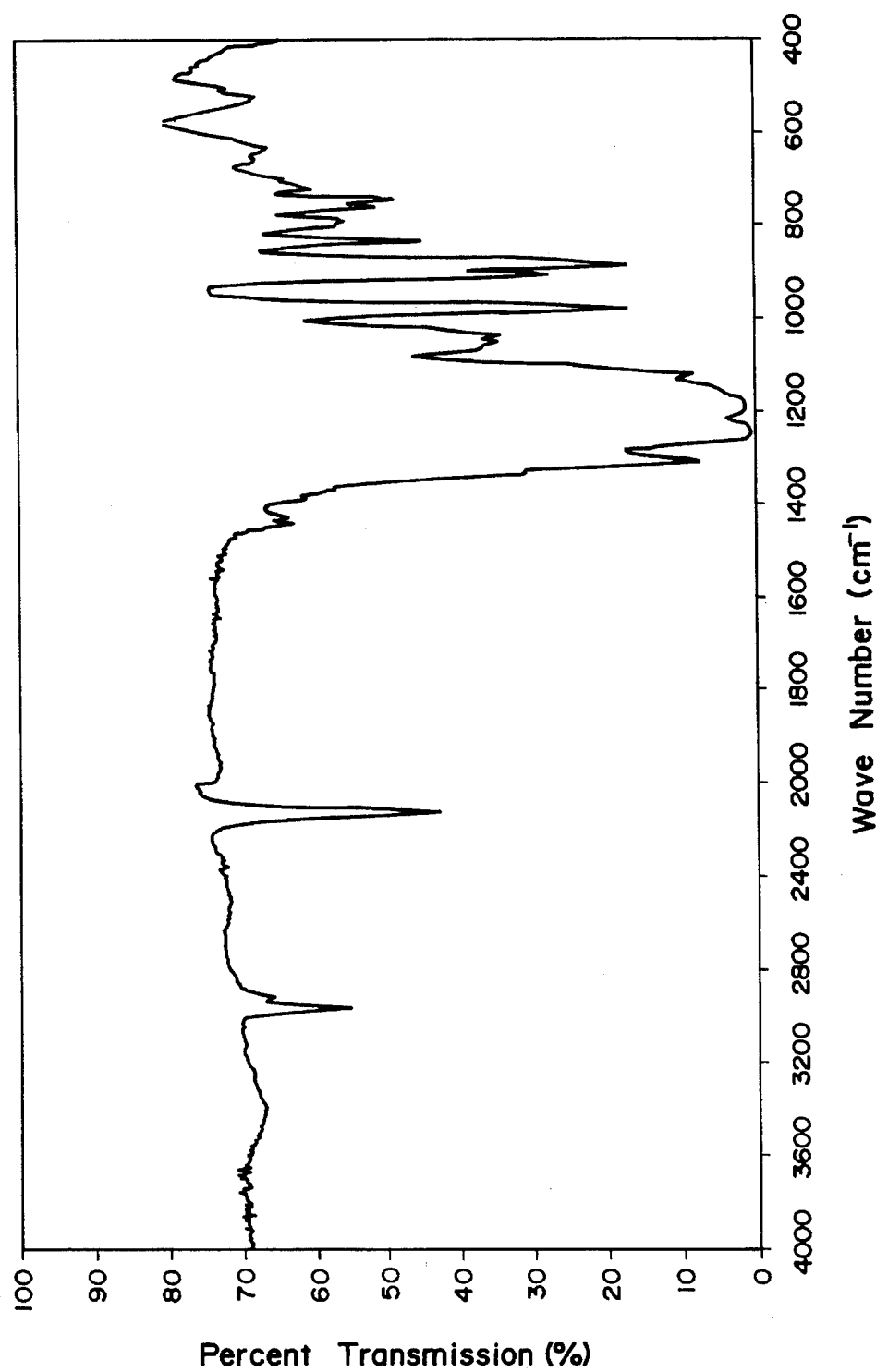
FIG. 1 is an IR spectrum of the fluorinated organosilicon compound of the present invention synthesized in Example 1.

The above fluorinated organic group Rf in the present invention is preferably a divalent perfluoropolyether group. Its preferable examples are those illustrated below:

$-(CF_2)_4-, \quad -(CF_2)_6-, \quad -(CF_2)_8-$ $$\begin{array}{c} -(CFOCF_2)_2(CF_2OCF)_2- \\ | \quad\quad\quad | \\ CF_3 \quad\quad\quad CF_3 \end{array}$$

$$\begin{array}{c} -(CFOCF_2)_3(CF_2OCF)_2- \\ | \quad\quad\quad | \\ CF_3 \quad\quad\quad CF_3 \end{array}$$

$$\begin{array}{c} -CF_2(CFOCF_2)_4(CF_2OCF)_4-CF_2- \\ | \quad\quad\quad\quad | \\ CF_3 \quad\quad\quad\quad CF_3 \end{array}$$

$$\begin{array}{c} -(CFOCF_2)_2(CF_2)_2(CF_2OCF)_2- \\ | \quad\quad\quad\quad | \\ CF_3 \quad\quad\quad\quad CF_3 \end{array}$$

$$\begin{array}{c} -(CFOCF_2)_3(CF_2)_3(CF_2OCF)_2- \\ | \quad\quad\quad\quad | \\ CF_3 \quad\quad\quad\quad CF_3 \end{array}$$

$$\begin{array}{c} -CF_2CF_2OCF_2CFOCF_2(CF_2)_2CF_2OCFCF_2OCF_2CF_2- \\ | \quad\quad\quad\quad\quad | \\ CF_3 \quad\quad\quad\quad\quad CF_3 \end{array}$$

Thus, the following are typical examples for the fluorinated organosilicon compound of the present invention.

$$\begin{array}{cc} CH_3 & CH_3 \\ | & | \\ H-SiCH_2CH_2(CF_2)_4-CH_2CH_2Si-H \\ | & | \\ CH_3 & CH_3 \end{array}$$

$$\begin{array}{cc} CH_3 & CH_3 \\ | & | \\ H-SiCH_2CH_2(CF_2)_6-CH_2CH_2Si-H \\ | & | \\ CH_3 & CH_3 \end{array}$$

$$\begin{array}{cc} CH_3 & CH_3 \\ | & | \\ H-SiCH_2CH_2(CF_2)_8-CH_2CH_2Si-H \\ | & | \\ CH_3 & CH_3 \end{array}$$

$$\begin{array}{cccc} CH_3 & & & CH_3 \\ | & & & | \\ H-SiCH_2CH_2-(CFOCF_2)_2(CF_2OCF)_2-CH_2CH_2Si-H \\ | & | & | & | \\ CH_3 & CF_3 & CF_3 & CH_3 \end{array}$$

-continued

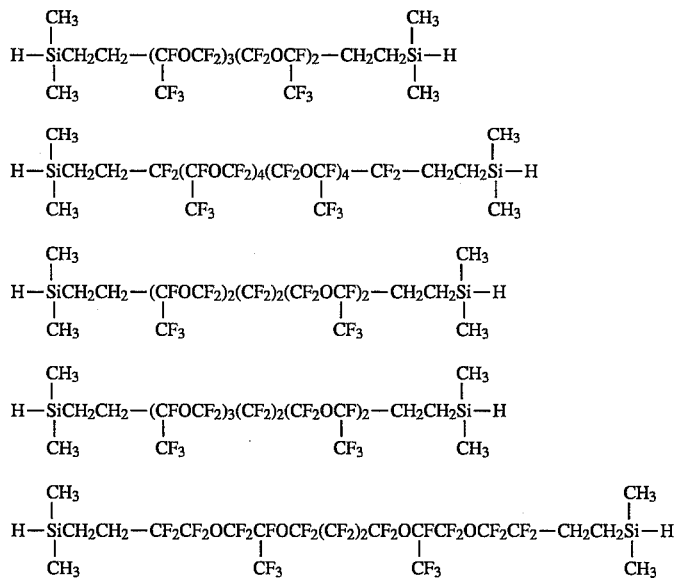

The fluorinated organosilicon compound of the present invention may be synthesized by treating, with a reducing agent, a doubly-silyl-terminated perfluoropolyether or a doubly-silyl-terminated perfluoropolyalkylene represented, for example, by general formula (3) below:

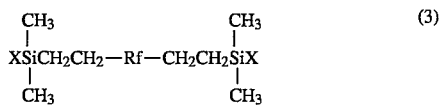

wherein X represents a halogen atom, F, Cl, Br, or I and Rf has the same meaning as previously defined.

The reaction of a polyether or polyalkylene of general formula (3) above may be readily carried out by suspending or dissolving a reducing agent in a nonaqueous solvent, and adding dropwise the polyether or polyalkylene of general formula (3) above. Suitable reducing agents to be used are lithium aluminum hydride, sodium borohydride, and the like, usually used in amounts of ¼–3 times, preferably about ½—about equimolar amounts with respect to the terminal group X of the compound or general formula (3) above. Suitable nonaqueous solvents are dehydrated nonaqueous solvents, such as THF, diethylether, 1,3-dimethyl-2-imidazolidinone (DMI), dimethylformamide (DMF), dimethylsulfoxide (DMSO), and the like. If the reaction, which for the most part proceeds rapidly even at room temperature, is slow, it should be heated to a suitable temperature ranging from 40°–100° C.

The fluorinated organosilicon compounds of the present invention may be used in a variety of applications. For example, treating a double-unsaturation-terminated perfluoropolyether or perfluoropolyalkylene, for example, as represented by the following general formula:

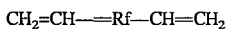

(Rf is as previously defined) with a fluorinated organosilicon compound of the present invention in the presence of an addition reaction catalyst will lead to the synthesis of a polymer with a main chain containing perfluoropolyether groups or perfluoropolyalkylene groups. The polymer is useful as a material for highly solvent-resistant and chemical-resistant rubber because the polymer has a high fluorine content, and particularly as a material which may be used as a mold release because the polymer has a low surface energy.

EXAMPLES

The present invention is illustrated in more detail by reference to the following examples.

Example 1

To a 100 ml three-neck flask provided with a stirrer, a thermometer, a Dimroth condenser, and a dropping funnel through which nitrogen gas was introduced at a rate of 50 ml/min were added 0.38 g of lithium aluminum hydride and 10 g of THF, followed by adding dropwise, while stirring the contents with a stirrer, 10.7g of a doubly-dichlorosilyl-terminated perfluoropolyether represented by the following formula:

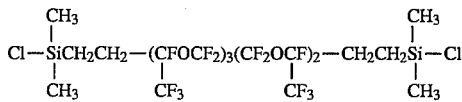

After completing the addition, the mixture was allowed to stand for 30 minutes at room temperature and after filtering off the unchanged lithium aluminum hydride, it was vacuum distilled to give 8.3 g of a fraction boiling at 117° C./1 mmHg.

The distillate fraction was analyzed by elemental analysis, IR, $^1$H-NMR, $^{19}$F-NMR, and GC-MASS. The results are given below.

GC-MASS: Molecular weight=1,004 IR: The spectrum is provided in FIG. 1: $v_{Si-H}$: 2,130 cm$^{-1}$ $v_{C-F}$: 1,100–1,300 cm$^{-1}$ $^1$H-NMR: TMS Standard, ppm 0.13 (d, Si—CH$_3$, 12H) 0.83 (m, Si—CH$_2$, 4H) 2.20 (m, CF—CH$_2$, 4H) 3.93 (m, Si—H, 2H) $^{19}$F-NMR: CF$_3$ COOH Standard, ppm

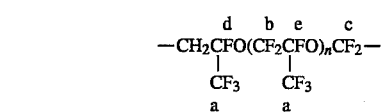

a: −3.60
b: −6.19
c: −9.36
d: −52.05
e: −67.87

| Elemental Analysis: | | | | | |
|---|---|---|---|---|---|
| | C % | H % | Si % | F % | O % |
| Calculated | 27.5 | 2.2 | 5.5 | 56.8 | 8.0 |
| Found | 27.8 | 1.9 | 5.1 | 56.7 | 8.5 |

The above analytical results show the distillate fraction to be a compound of the following structural formula.

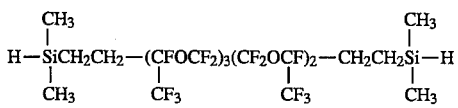

Example 2

To a 100 ml three-neck flask provided with a stirrer, a thermometer, a Dimroth condenser, and a dropping funnel through which nitrogen gas was introduced at a rate of 50 ml/min were added 0.38 g of lithium aluminum hydride and 10 g of THF, followed by adding dropwise, while stirring the contents with a stirrer, 9.1 g of a doubly-dichlorosilyl-terminated perfluoropolyether represented by the following formula:

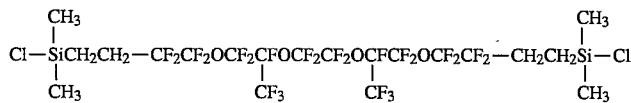

After completing the addition, the mixture was allowed to stand for 30 minutes at room temperature and after filtering off the unchanged lithium aluminum hydride, it was vacuum distilled to give 6.9 g of a fraction boiling at 108° C./1 mmHg.

Figure 2:
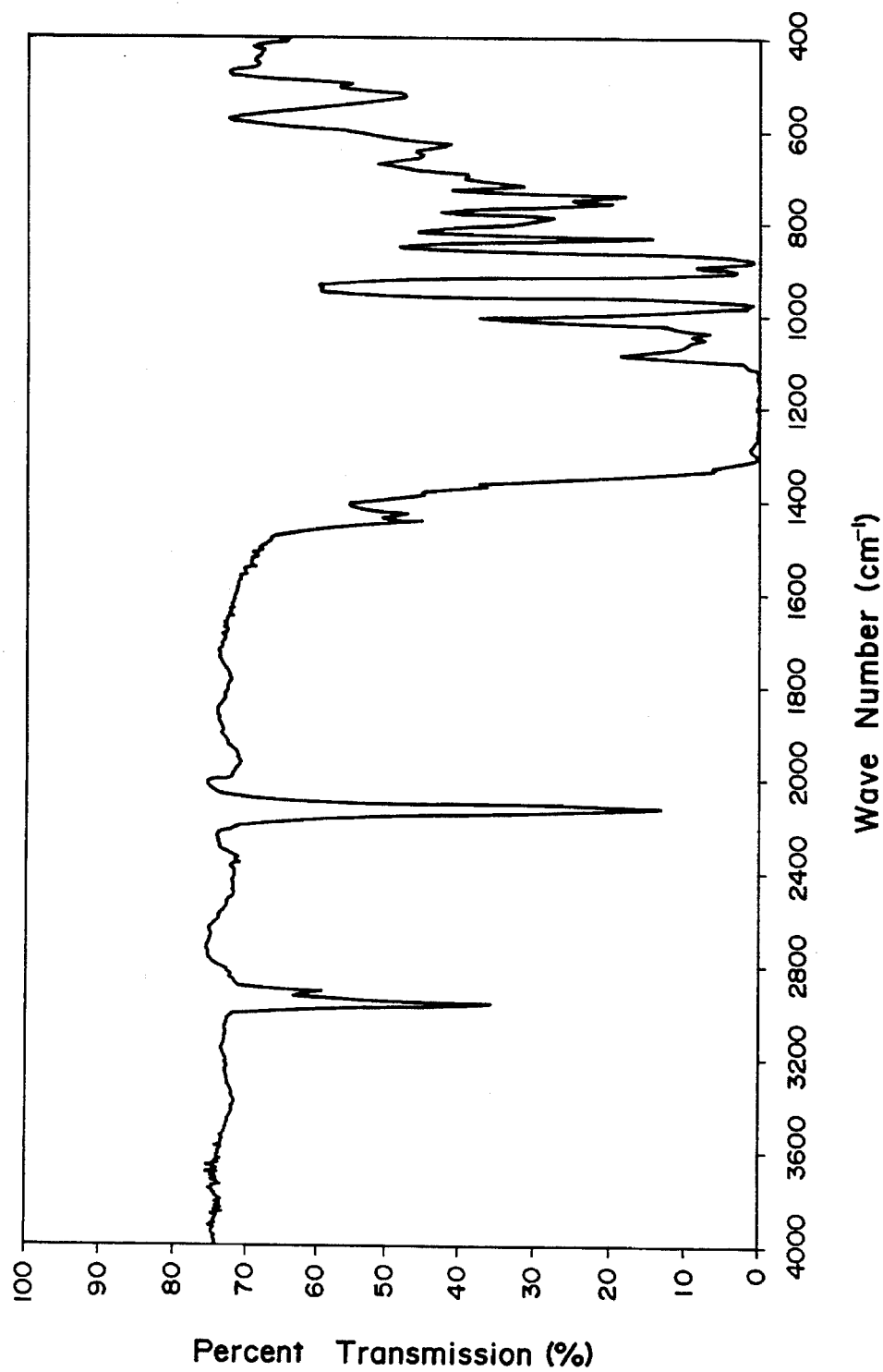
FIG. 2 is an IR spectrum of the fluorinated organosilicon compound of the present invention synthesized in Example 2.

The distillate fraction was analyzed in a manner similar to that of Example 1 to give the following results:

GC-MASS: Molecular weight=838 IR: The spectrum is provided in FIG. 2: $\nu_{Si-H}$: 2,130 cm$^{-1}$ $\nu_{C-F}$: 1,100–1,300 cm$^{-1}$ $^1$H-NMR: TMS Standard, ppm 0.14 (d, Si—CH$_3$, 12H) 0.85 (m, Si—CH$_2$, 4H) 2.21 (m, CF—FH$_2$, 4H) 3.95 (m, Si—H, 2H) $^{19}$F-NMR: CF$_s$COOH Standard, ppm

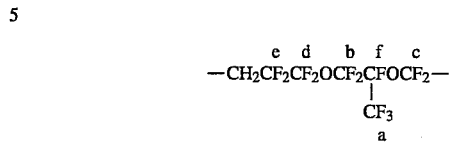

a: −3.93
b: −4.81
c: −9.35
d: −10.78
e: −43.11
f: −68.07

| Elemental Analysis: | | | | | |
|---|---|---|---|---|---|
| | C % | H % | Si % | F % | O % |
| Calculated | 28.7 | 2.6 | 6.7 | 54.4 | 7.6 |
| Found | 28.9 | 2.3 | 6.7 | 55.0 | 7.1 |

The above analytical results show the distillate fraction to be a compound of the following structural formula.

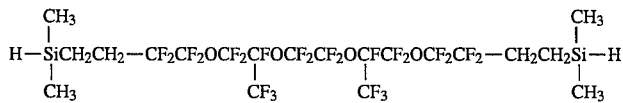

Example 3

To a 100 ml three-neck flask provided with a stirrer, a thermometer, a Dimroth condenser, and a dropping funnel through which nitrogen gas was introduced at a rate of 50 ml/min were added 0.76 g of lithium aluminum hydride and 10 g of THF, followed by adding dropwise, while stirring the contents with a stirrer, 10.8 g of a doubly-dichlorosilyl-terminated perfluoropolyalkylene represented by the following formula:

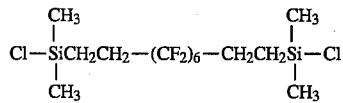

After completing the addition, the mixture was allowed to stand for 30 minutes at room temperature, and after filtering off the unchanged lithium aluminum hydride, it was vacuum distilled to give 7.0 g of a fraction boiling at 121° C./4 mmHg.

The distillate fraction was analyzed in a manner similar to that of Example 1 to give the following results.

Figure 3:
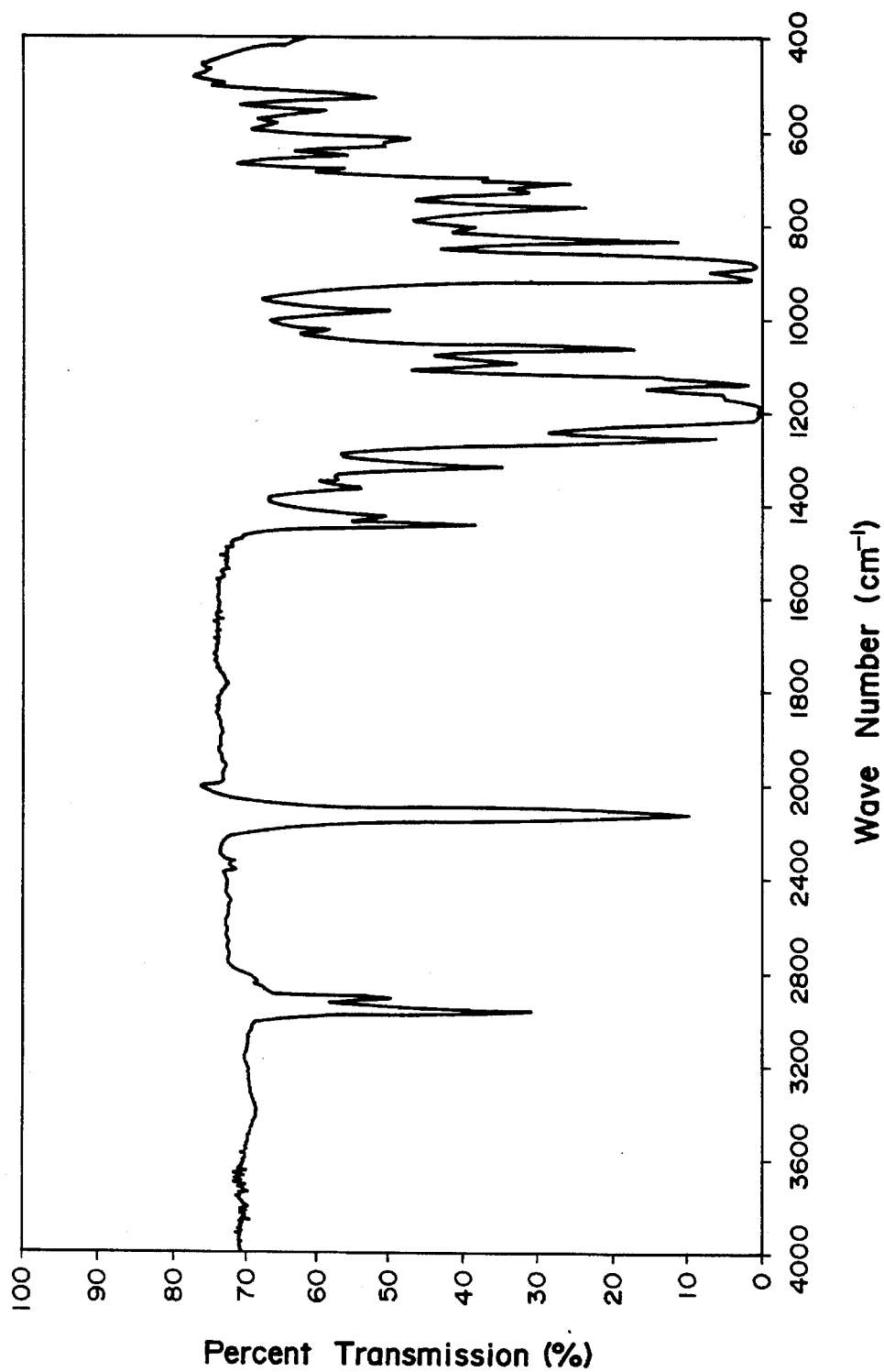
FIG. 3 is an IR spectrum of the fluorinated organosilicon compound of the present invention synthesized in Example 3.

GC-MASS: Molecular weight=474 IR: A spectrum is provided in FIG. 3: $v_{Si-H}$: 2,130 cm$^{-1}$ vc—F: 1,100–1,300 cm$^{-1}$ $^1$H-NMR: TMS Standard, ppm 0.16 (d, Si—CH$_3$, 12H) 0.88 (m, Si—CH$_2$, 4H) 2.22 (m, CF—FH,, 4H) 3.96 (m, Si—H, 2H) $^{19}$F-NMR: CF$_3$COOH Standard, ppm

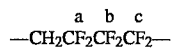

a: −38.42
b: −44.28
c: −45.80

|  | Elemental Analysis: | | | |
| --- | --- | --- | --- | --- |
|  | C % | H % | Si % | F % |
| Calculated | 35.4 | 4.6 | 11.8 | 48.2 |
| Found | 35.6 | 4.3 | 12.1 | 48.0 |

The above analytical results show the distillate fraction to be a compound of the following structural formula.

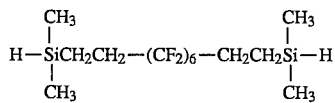

Because the novel fluorinated organosilicon compound of the present invention has two silylethylene groups having a structure that a Si atom is linked, through an ethylene group, to a divalent perfluoroalkylene group or a divalent perfluoroether group, they exhibit excellent properties, such as solvent resistance, chemical resistance, and mold release, and materials prepared from these polymers, such as a variety of rubbers, show improvements in these properties.

What is claimed is:

1. A fluorinated organosilicon compound represented by formula (1):

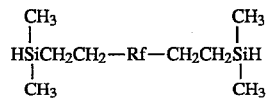

wherein Rf is a divalent group represented by formula (2):

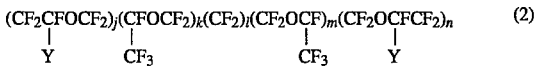

wherein Y is a fluorine atom or a CF$_3$ group, l is an integer of 0–8; k and m are integers of 0–4; j and n are integers of 0 or 1; with the proviso that the integers j, k, m, and n cannot be simultaneously equal to zero.

2. The organosilicon compound of claim 1, wherein Rf is a divalent perfluoropolyether group.

3. The organosilicon compound of claim 1, wherein Rf is

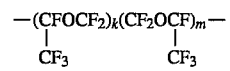

wherein k and m are integers of 0–4; except when k=m=0.

4. The organosilicon compound of claim 1, wherein Rf is

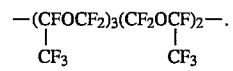

5. The organosilicon compound of claim 1, wherein Rf is

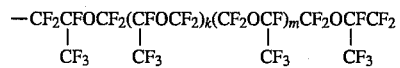

wherein k and m are integers of 0–4.

6. The organosilicon compound of claim 1, wherein Rf is

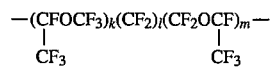

wherein k and m are integers of 0–4; and l is an integer of 1–8.

7. The organosilicon compound of claim 1, wherein Rf is

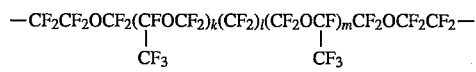

wherein k and m are integers of 0–4; and l is an integer of 0–8.

* * * * *

UNITED STATES PATENT AND TRADEMARK OFFICE
CERTIFICATE OF CORRECTION

PATENT NO. : 5,475,078
DATED : Dec. 12, 1995
INVENTOR(S) : Shinichi Sato et al.

It is certified that error appears in the above-indentified patent and that said Letters Patent is hereby corrected as shown below:

Column 8,

Claim 6, in the formula, change "$CFOCF_3$" to -- $CFOCF_2$ --

Signed and Sealed this

Twenty-first Day of May, 1996

Attest:

BRUCE LEHMAN

Attesting Officer        Commissioner of Patents and Trademarks